United States Patent [19]

Lutz

[11] Patent Number: 5,087,419
[45] Date of Patent: Feb. 11, 1992

[54] OZONE STERILIZATION PROCESS WHICH DECONTAMINATES EVACUATED WASTE WITH OZONE

[75] Inventor: George H. Lutz, Binghamton, N.Y.

[73] Assignee: Northeast Air/Water Corporation, Binghamton, N.Y.

[21] Appl. No.: 473,555

[22] Filed: Feb. 1, 1990

[51] Int. Cl.$^5$ .......................... B01J 19/08; B01J 19/12
[52] U.S. Cl. ........................................ 422/28; 422/33; 422/32; 422/186.07; 422/186.03
[58] Field of Search ...................... 422/28, 24, 32, 31, 422/33, 186.07, 186.30

[56] References Cited

U.S. PATENT DOCUMENTS

| 4,156,652 | 5/1979 | Wiest | 422/186.07 |
| 4,793,931 | 12/1988 | Stevens et al. | 422/186.3 |
| 4,988,484 | 1/1991 | Karlson | 422/186.07 |

Primary Examiner—David L. Lacey
Assistant Examiner—Thomas E. Daley
Attorney, Agent, or Firm—Salzman & Levy

[57] ABSTRACT

The invention features an apparatus and method of detoxifying and/or sterilizing waste materials utilizing ozone under pressure. The waste materials are loaded into a pressurizable chamber in which the ozone is introduced under pressure. The ozone penetrates and sterilizes and waste materials, after which the gas is evacuated from the chamber following a given treatment cycle. The evacuated gas is then fed to a second, purification chamber. Any toxic substances or contaminants that may have been released in the first waste chamber and were carried along with the evacuated gas are further purified. This is accomplished by introducing ozone into the second chamber to mix with and sterilize the evacuated waste gases. This second introduction of the ozone to purify the waste gases is an essential step of the process, and ensures that none of the toxic or contaminating substances escape to the environment.

6 Claims, 3 Drawing Sheets

OZONE STERILIZATION PROCESS WHICH DECONTAMINATES EVACUATED WASTE WITH OZONE

FIELD OF THE INVENTION

The present invention relates to a process and apparatus for detoxifying waste utilizing ozone under pressure, and more particularly to an apparatus and process therefor that injects ozone under pressure to a chamber in which toxic waste has been introduced.

BACKGROUND OF THE INVENTION

In recent times, there has been a proliferation of toxic waste and other infectious materials from various hospitals and health centers, including clinics and doctors' offices across the country. At present, there is no easy way of disposing of these materials.

Last year, toxic waste was illegally dumped in landfills, empty lots, and in the ocean. On the shores of New Jersey, beaches were contaminated and rendered uninhabitable by toxic waste washing-up on the shore. This caused such consternation among local residents and governing officials that laws were quickly enacted to monitor and tag these offensive materials, and thereby assure their safe, proper and legal disposal.

The need to tag and monitor these waste is both time consuming and expensive. Clearly, there has developed a need to detoxify biological and medical waste at their source, wherein tagging and monitoring will become unnecessary.

Unfortunately, there is no cost-effective and efficacious means of detoxifying waste in medical laboratories, hospitals and physicians' offices at the present time.

SUMMARY OF THE INVENTION

The invention features an apparatus and method of detoxifying and/or sterilizing waste materials utilizing ozone under pressure. The waste materials are loaded into a pressurizable chamber in which the ozone is introduced under pressure. The ozone penetrates and sterilizes the waste materials, after which the gas is evacuated from the chamber following a given treatment cycle. The evacuated gas is then fed to a second, purification chamber.

Any toxic substances or contaminants that may have been released in the first waste chamber and were carried along with the evacuated gas are further purified. This is accomplished by introducing ozone into the second chamber to mix with, and sterilize the evacuated waste gases. This second introduction of the ozone to purify the waste gases is an essential step of the process, and ensures that none of the toxic or contaminating substances escape to the environment.

It is also useful to mix the waste materials in the first chamber during detoxification, so that ozone penetration into the waste materials is enhanced. This mixing step is not necessary for smaller quantities of waste, in accordance with an alternate embodiment of the invention The process is controlled by a programmed microprocessor, which controls the sterilization cycles, i.e., the time of introduction and evacuation of both first and second chambers. The effective duration of any ozone cycle will vary with temperature and pressure as well as with the size of the waste load. An average load size will usually be substantially decontaminated in about 20 minutes to one hour. An average load will range from approximately one to eight pounds.

The first chamber is equipped with a biasing switch for the lid used to introduce the waste materials. This biasing ensures that the lid is in a locked position after the chamber has been filled with waste. The switch controls the initialization of the computer program controlling the ozone cycles, and acts as a safety device wherein the system process cannot be started unless the first chamber is absolutely sealed.

It is an object of the present invention to provide a simple, inexpensive apparatus and method for detoxifying medical waste materials at their source.

It is another object of the present invention to provide an improved apparatus and method for detoxifying such infectious waste materials.

It is another object of this invention to decontaminate waste materials using a double ozone introduction process.

BRIEF DESCRIPTION OF THE DRAWINGS

These and other objects of the invention will be better understood and will become more apparent with reference to tho subsequent detailed description considered in conjunction with the accompanying drawing, in which.

DESCRIPTION OF THE PREFERRED EMBODIMENT

Generally speaking, the invention pertains to a method and apparatus for detoxifying waste materials, such as medical waste and other bacterially-contaminated materials.

Ozone is generated and introduced under pressure to a chamber containing the target materials to be decontaminated. Effluent (waste treatment) gas, not shown, resulting from the decontamination process is purged from the chamber after the sterilization cycle. Ozone is now introduced to a second chamber containing the effluent gas in order to purify any contaminants contained therein.

Figure 1:
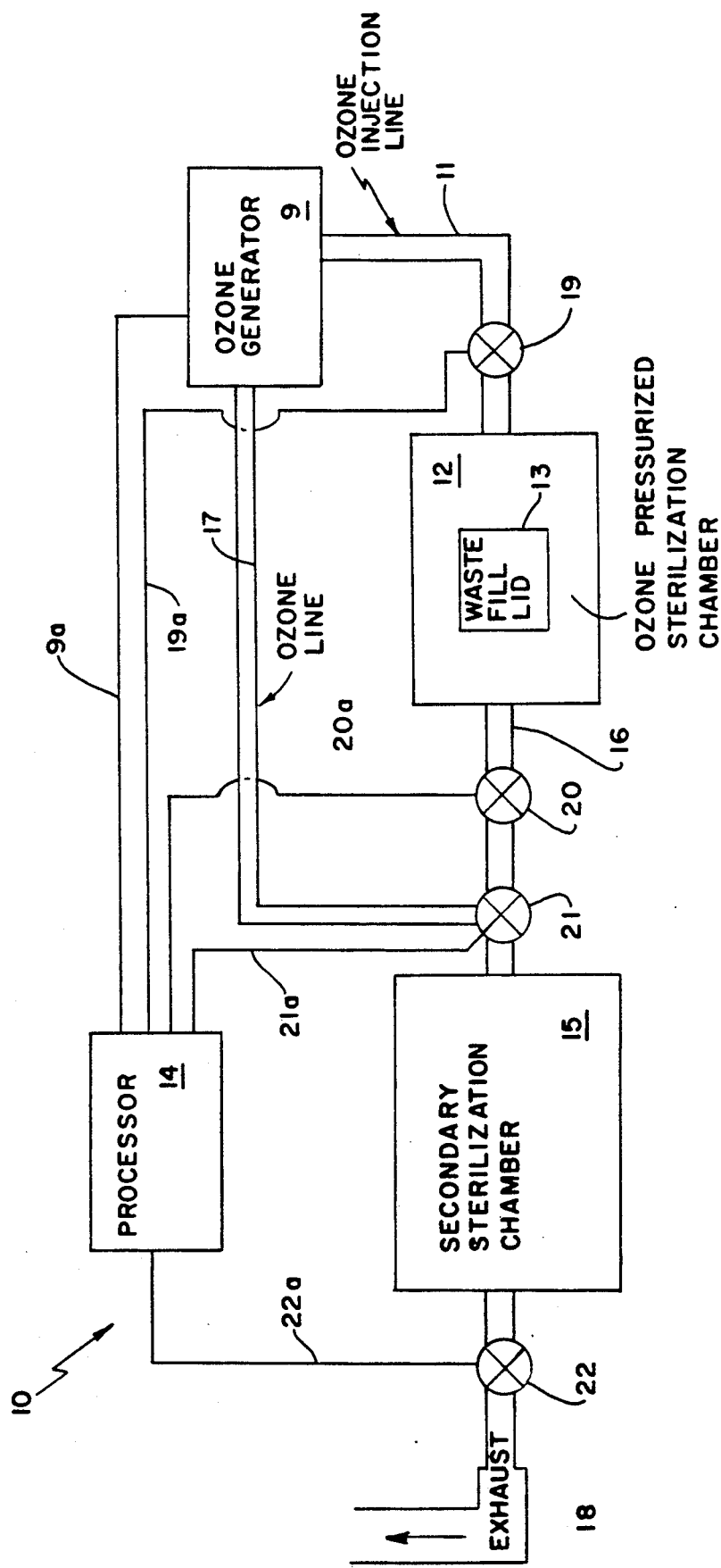
FIG. 1 is a schematic diagram of the apparatus of the invention.

Now referring to FIG. 1, a schematic diagram is illustrated for the commercial apparatus 10 of this invention.

The apparatus 10 comprises an ozone generator 9, which is manufactured by Northeast Air/Water Research Corp. (NEAWR) Binghamton, N.Y., as Model No. 100-0. The ozone generator 9 injects the generated ozone, not shown, into conduit 11, which feeds into a motorized, barrel-shaped pressure mixing chamber 12, having interior ribs, such as is available as Model No. 1000-P manufactured by NEAWR Corp. Chamber 12 is for receiving toxic and contaminated waste materials, not shown.

Chamber 12 has a waste-fill lid 13, suitably hinged to the chamber housing 12 which opens to allow for the introduction of contaminated waste materials into chamber 12. Lid 13 includes a biased switch (not shown), which allows the lid to be positively sealed, enabling the initialization of a computer processing program, not shown, contained in a processor 14, which may be a PC, such as is available from the Hewlett-Packard Company, or a dedicated control processor well known in the art.

Connected to pressurized sterilization mixing chamber 12 by means of a conduit 16 and intermediary value 20, is a secondary sterilization chamber 15. Secondary sterilization chamber 15 is adapted to receive effluent gases from mixing chamber 12 and to receive ozone from generator 9 by means of conduit 17 and valve 21. The output of secondary sterilization chamber 15 is vented to an exhaust conduit 18 by means of valve 22.

Conduits 11, 16, 17 and 18 are regulated by respective microprocessor valves 19, 20, 21 and 22, such as are manufactured by Advanced Pressure Products Company, Ithaca, N.Y., in accordance with processor cycle control signals, not shown, that are generated by the computer program Appropriate electrical signal lines, 19a, 20a, 21a and 22a connect the processor 14 to each valve 19, 20, 21 and 22 in a manner well known to those of ordinary skill in the art.

Figure 2:
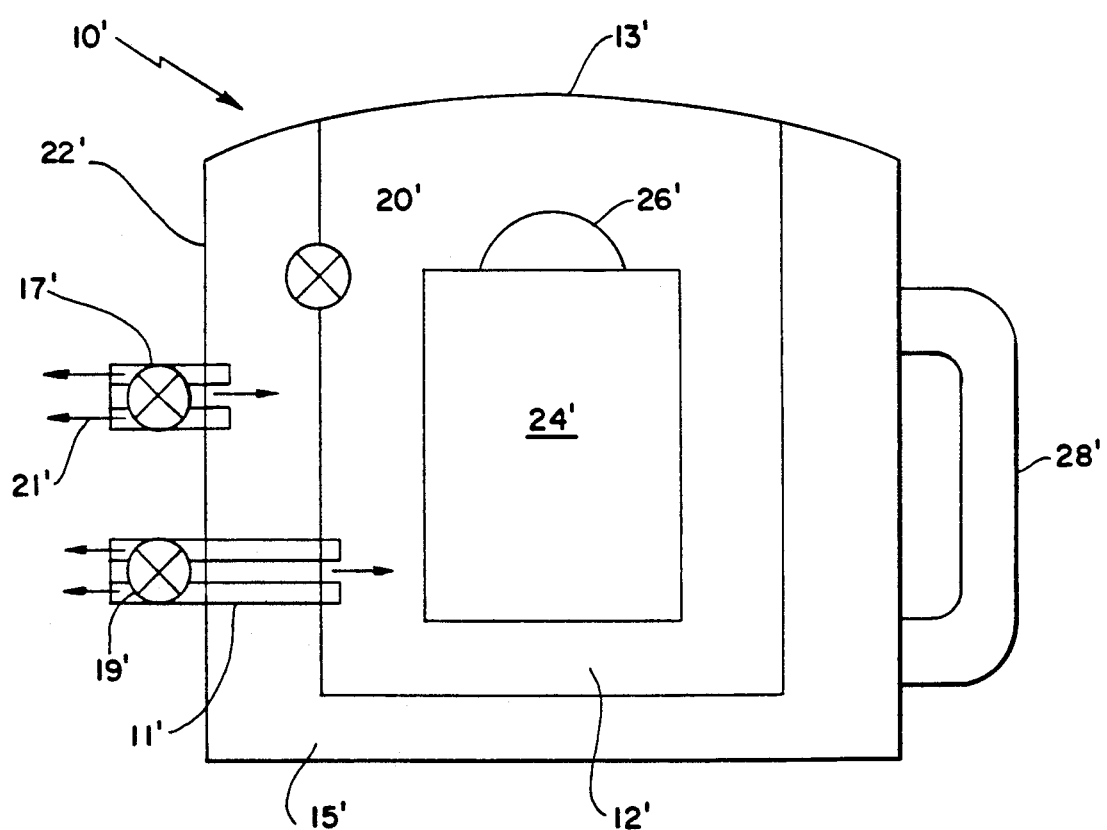
FIG. 2 is a schematic diagram of an alternate embodiment of the inventive apparatus.

Now referring to FIG. 2, a schematic diagram is illustrated for an alternate embodiment of the apparatus 10' of this invention. This embodiment is a smaller system than the commercial apparatus 10 described hereinabove with reference to FIGURE 1, and is intended for use in physician's offices for detoxifying smaller quantities of waste.

The apparatus 10' is also computer processor-controlled and comprises an ozone generator, not shown, which can be connected thereto by means of quick-connect ports 11' and 17'. A 1 gallon, mug-shaped housing 22', such as is manufactured by NEAWR Corp., consists of a secondary sterilization chamber 15' surrounding a pressure chamber 12'. Unlike chamber 12 (FIG. 1), chamber 12' is neither ribbed nor motorized, as smaller quantities of waste material need not be mixed during the sterilization cycle.

Chamber 12' has a waste-fill lid 13', suitably hinged to the chamber housing 12' which opens to allow for the introduction of contaminated waste materials basket 24' and thence into chamber 12'. A removable, perforated plastic or stainless steel basket 24', having a handle 26' attached to it, contains waste and is disposed in chamber 12'. Lid 13' includes a biased switch (not shown), which allows the lid to be positively sealed, enabling the initialization of a computer processing program, not shown, contained in a processor, which may be a PC, such as is available from the Hewlett-Packard Company, or dedicated control processor well known in the art. A handle 28' is provided to allow the housing 22' to move from office to office or room to room within a medical facility.

Connected to the inner pressurized sterilization chamber 12' by means of a conduit intermediary valve 20', is an outer, secondary sterilization chamber 15'. Secondary sterilization chamber 15' is adapted to receive effluent gases from chamber 12' and to receive ozone from the ozone generator via port 17' and bidirectional valve 21'. The output of secondary sterilization chamber 15' is vented to an exhaust conduit, not shown, via bidirectional valve 21'.

Figure 3:
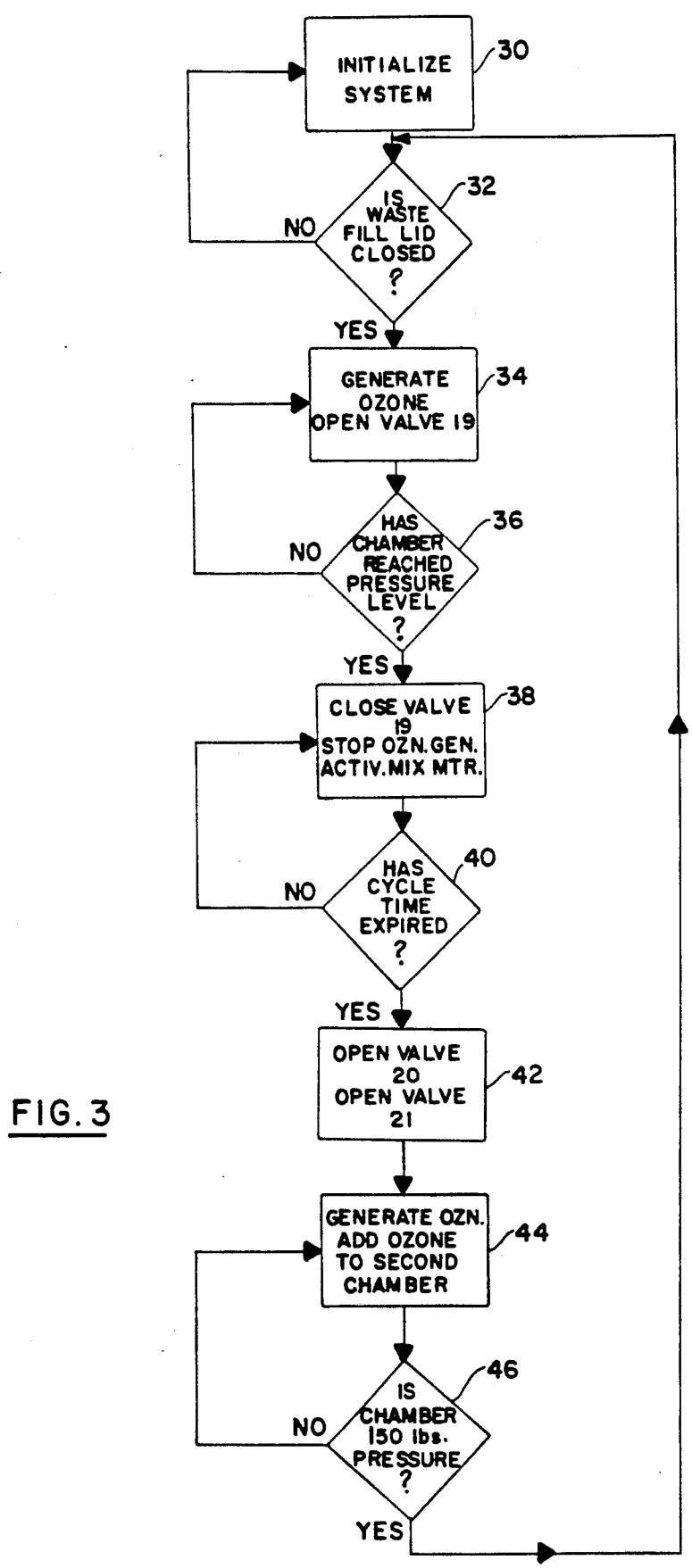
FIG. 3 is a flow chart of computer processor operation.

Referring now also to FIG. 3, a computer processing program residing in processor 14 is depicted in a flow chart. For simplicity, the apparatus depicted in FIG. 1 is referred to hereinafter, but it should be understood that the computer-controlled method described herein is equally applicable with respect to the apparatus depicted in FIGURE 2.

The processor 14 starts the ozone generator 9, step 34, and continues to operate the generator in accordance with a selected ozone treatment cycle. The operator of the apparatus 10 enters in the requested variables such as: ozone quantity, load and pressure, and the program automatically selects the applicable ozone treatment cycle time and waste mixing cycle time for the ozone generator 9 and chamber 12, respectively. Of course, some or all of the aforementioned parameters may be measured during operation by appropriate sensors, not shown, rather than humanly entered or calculated. Moreover, other sensors, not shown, may be incorporated to detect the level of virulent bacteria in the chamber 12.

In the preferred embodiment, sterilization chamber 12 contains between 5 and 50 lbs. of pressure, dependent on waste type and quantity. The aforementioned processor program also regulates the ozone pressure during the ozone treatment cycle. For chamber 12' (FIG. 2), a gas pressure of between 5 and 20 lbs. is sufficient.

added to the chamber 12 and detoxified by the addition of the ozone to the chamber in accordance with the ozone generating treatment cycle, steps 34–40, effluent gases are exhausted to secondary sterilization chamber 15, step 42, via conduit 16. In the case of the apparatus depicted in FIG. 2, however, the step of activating the mixing motor, step 38, is of course, omitted, as no motor is included in housing 22'.

The processor 14 then initiates a second ozone generating cycle, step 44, in which ozone is fed to secondary sterilization chamber 15 via conduit 17 and valve 21, to purify or otherwise decontaminate the effluent gases. The pressure in secondary sterilization chamber 15 is necessarily less than the pressure in sterilization chamber 12. Nominally, the secondary sterilization chamber 15 contains approximately 5 lbs. of pressure before effluent gases are added hereto. In the apparatus of FIG. 2, however, between 1 and 5 lbs. of pressure is sufficient for secondary sterilization chamber 15'.

The detoxified effluent gases are exhausted, step 46, via valve 22 and conduit 18 when the effluent gases move from sterilization chamber 12 to secondary sterilization chamber 15. When secondary sterilization chamber pressure reaches approximately 0 lbs., step 50, valves 20, 21 and 22 are closed.

For typical commercial waste loads of between 10 and 50 pounds, and treatment cycle times ranging from 20 minutes to 2 hours in duration, pressures will typically range from 5 to 50 pounds per square inch gauge (psig).

The following examples are illustrative of the process described above.

EXAMPLE 1

Eleven ounces of biological waste consisting of contaminated meat, having a virulent contaminant of $1.2 \times 10^{10}$ standard plate count (SPC) per gram was placed in a 1.0 cubic foot chamber manufactured by the NEAWR corporation as Model No. 1000-P. The aforementioned NEAWR ozone generator Model No. 100-O introduced 1 gram of ozone into the chamber at a pressure of 20 psig. The material remained in the sterilization chamber for 1 hour, during the ozone penetrating and sterilizing cycle. At the conclusion of this cycle, gas was evacuated from the sterilization chamber. The result of this experiment was sterilization of waste material to a virulent bacteria level of $9.4 \times 10^6$ SPC/gm, representing a successful sterilization rate of over 99.92%.

EXAMPLE 2

Eleven ounces of biological waste consisting of contaminated meat, having a virulent contaminant of $2.5 \times 10^7$ SPC/gm was placed in a 1.0 cubic foot chamber manufactured by the NEAWR corporation as Model No. 1000-P. The aforementioned ozone generator Model No. 100-O introduced 1 gm of ozone into the chamber at a pressure of 20 psig. The material remained in the sterilization chamber for 30 minutes, during the ozone penetrating and sterilizing cycle. At the conclusion of this cycle, gas was evacuated from the sterilization chamber. The result of this experiment was sterilization of waste material to a virulent bacteria level of $2.4 \times 10^7$ SPC/gm, representing a successful sterilization rate of only 4%.

EXAMPLE 3

Eleven grams of biological waste consisting of contaminated meat, having a virulent contaminant of $1.2 \times 10^{10}$ SpC per gram was placed in a 1.0 cubic foot chamber manufactured by the NEAWR corporation as Model No. 1000-P. The aforementioned NEAWR ozone generator Model No. 100-O introduced 1 gram of ozone into the chamber at a pressure of 20 psig. The material remained in the sterilization chamber for 1 hour, during the ozone penetrating and sterilizing cycle. At the conclusion of this cycle, gas was evacuated from the sterilization chamber. The result of this experiment was sterilization of waste material to a virulent bacteria level of $9.4 \times 10^6$ SPC/gm.

EXAMPLE 4

Eleven grams of biological waste consisting of contaminated meat having a virulent contaminant of $2.5 \times 10^7$ SPC/gm was placed in a 1.0 cubic foot chamber manufactured by the NEAWR corporation as Model No. 1000-P. The aforementioned ozone generator Model No. 100-O introduced 1 gm of ozone into the chamber at a pressure of 20 psig. The material remained in the sterilization chamber for 30 minutes during the ozone penetrating and sterilizing cycle. At the conclusion of this cycle, gas was evacuated from the sterilization chamber. The result of this experiment was sterilization of waste material to a virulent bacteria level of $2.4 \times 10^7$ SPC/gm.

EXAMPLE 5

Eleven ounces of biological waste consisting of contaminated meat, having a virulent contaminant of $1.2 \times 10^{10}$ SPC per gram was placed in a 1.0 cubic foot chamber manufactured by the NEAWR corporation as Model No. 1000-P. The aforementioned NEAWR ozone generator Model No. 100-O introduced 1 gram of ozone into the chamber at a pressure of 20 psig. The material remained in the sterilization chamber for 1 hour, during the ozone penetrating and sterilizing cycle. At the conclusion of this cycle, gas was evacuated from the sterilization chamber. The result of this experiment was substantially no sterilization of waste material, except for the outer surface of the mass under test The level of virulent bacteria remained at $1.2 \times 10^{10}$ SPC/gm.

Since other modifications and changes varied to fit particular operating requirements and environments will be apparent to those skilled in the art, the invention is not considered limited to the example chosen for purposes of disclosure, and covers all changes and modifications which do not constitute departures from the true spirit and scope of this invention.

Having thus described the invention, what is desired to be protected by Letters Patent is presented in the subsequently appended claims.

What is claimed is:

1. A method for sterilizing infectious waste material, the steps comprising:
    (a) loading and waste material into a pressurizable sterilization chamber;
    (b) introducing ozone gas under pressure into said sterilization chamber so as to penetrate and sterilize said waste material;
    (c) after a predetermined time cycle, evacuating gas from said sterilization chamber;
    (d) transferring said evacuated gas from said sterilization chamber into a purification chamber;
    (e) after said evacuated gas has been transferred into said purification chamber further introducing ozone gas into said purification chamber so as to sterilize said evacuated gas; and
    (f) removing said sterilized waste material from said sterilization chamber.

2. The method for sterilizing infectious waste material in accordance with claim 1, further comprising the step of:
    (g) controlling the generation and introduction of ozone gas by computer control means.

3. The method for sterilizing infectious, waste material in accordance with claim 2 wherein said ozone gas is introduced into said sterilization chamber is at a pressure of greater than 1.0 pound per square inch gauge.

4. The method for sterilizing infectious waste material in accordance with claim 2 wherein said predetermined time cycle is less than 2 hours.

5. The method for sterilizing infectious waste material in accordance with claim 2 wherein, said process steps (b) and (c) are controlled by computer control means.

6. The method for sterilizing infectious waste material in accordance with claim 1 wherein said waste material is mixed during said predetermined time cycle.

* * * * *